United States Patent [19]

Tam

[11] Patent Number: 5,182,261

[45] Date of Patent: Jan. 26, 1993

[54] MODIFIED TRANSFORMING GROWTH FACTOR ALPHA OLIGOPEPTIDES AND PHARMACEUTICAL COMPOSITIONS THEREOF

[75] Inventor: James P. Tam, New York, N.Y.

[73] Assignee: The Rockefeller University, New York, N.Y.

[21] Appl. No.: 379,332

[22] Filed: Jul. 13, 1989

[51] Int. Cl.[5] .................. A61K 37/36; C07K 7/10
[52] U.S. Cl. .................................. 514/12; 530/324; 530/350; 530/399
[58] Field of Search .................. 514/12; 530/324, 350, 530/399

[56] References Cited

U.S. PATENT DOCUMENTS

| | | | |
|---|---|---|---|
| 4,742,003 | 5/1988 | Derynck et al. | 530/350 |
| 4,764,504 | 8/1988 | Johnson et al. | 530/350 |
| 5,102,870 | 4/1992 | Florine et al. | 514/12 |

Primary Examiner—Lester L. Lee
Attorney, Agent, or Firm—Wyatt, Gerber, Burke & Badie

[57] ABSTRACT

This invention relates to transforming growth factor alpha modified by replacement of an L-amino acid residue with a D-amino acid residue and pharmaceutical compositions thereof useful in wound healing, ulcer treatment or trauma.

20 Claims, 3 Drawing Sheets

MODIFIED TRANSFORMING GROWTH FACTOR ALPHA OLIGOPEPTIDES AND PHARMACEUTICAL COMPOSITIONS THEREOF

This invention relates to transforming growth factor (TGFα), a physiologically active oligopeptide found in many mammalian body fluids and associated with the proliferation of normal cells. More particularly, it relates to modified TGF α compounds in which at least one of the amino acid residues is replaced with another residue, which may be another amino acid or the D-form of the same acid which, in the naturally occurring form of TGFα, is in the L-form. It is concerned also with pharmaceutical compositions containing a therapeutically effective amount of at least on modified TGFα to assist in the rapid proliferation of normal cells in wound healing, ulcer treatment or other trauma of mammals, particularly humans, with patients in need of such treatment.

Figure 1:
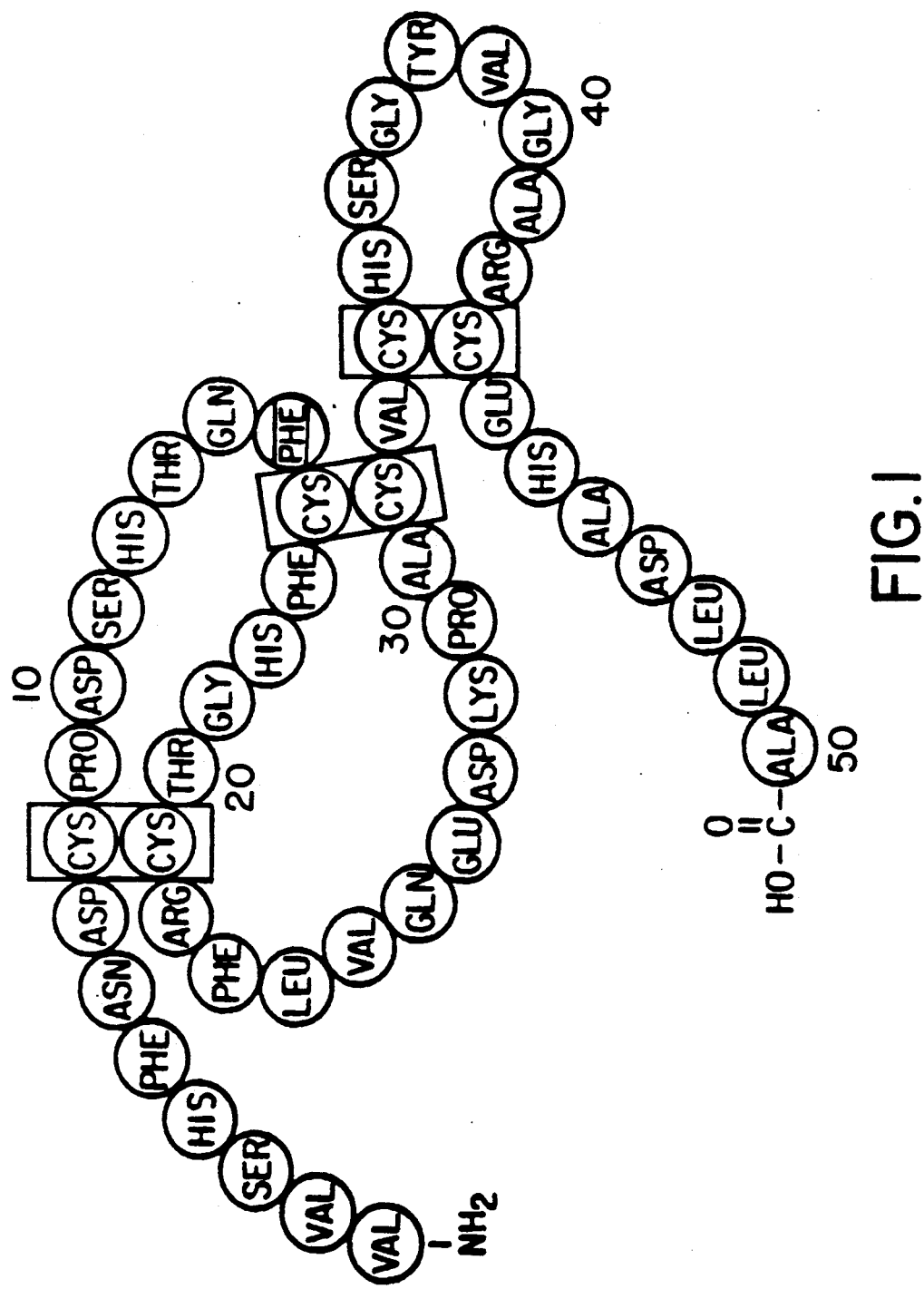

TGFα is one of a family of growth factors which include, amongst others, platelet derived growth factor, epidermal growth factor (EGF), nerve growth factor and fibroblast growth factor. The structure of the naturally occurring human TGFα is shown in FIG. 1. As will be seen, it is an oligopeptide containing 50 amino acid residues characterized by the presence of three disulfide bonds forming a tricyclic structure.

For convenience in describing the products of this invention standard abbreviations for the amino acids will be employed as shown in the following Table.

TABLE 1

| | |
|---|---|
| A = Ala = alanine | M = Met = methionine |
| C = Cys = cysteine | N = Asn = asparagine |
| D = Asp = aspartic acid | P = Pro = proline |
| E = Glu = glutanic acid | Q = Gln = glutamine |
| F = Phe = phenylalanine | R = Arg = arginine |
| G = Gly = glycine | S = Ser = serine |
| H = His = histidine | T = Thr = threonine |
| I = Il = isoleucine | V = Val = valine |
| L = Leu = leucine | W = Trp = tryptophan |
| | Y = Tyr = tyrosine |

The invention, as aforesaid, is concerned with modified TGFα in which at least one of the amino acid residues in FIG. 1 is replaced with another amino acid which may be a totally different amino acid or the D-form of the L-amino acid of the naturally occurring oligopeptide. In this specification and claims, the modified form of TGFα will be identified by the notation in parenthesis. For example, (D-Ser-3)TGFα represents a modified TGFα in which the L-Ser residue in the 3 position as shown in FIG. 1 has been replaced with a D-Ser. Similarly, (L-Ala-35)TGF is a modified TGFα in which L-His at the 35 position is replaced with L-Ala, (D-Phe-37)TGFα is a modified TGFα in which the Gly at the 37 position has been replaced with D-Phe. In (D-Phe-40) TGFα, the Gly at the 40 position has been replaced with D-Phe.

It has been observed that it is possible to increase or decrease the cell proliferation activity of TGFα by modifying the structure of the naturally occurring product in one of several ways. There are two steps involved in the physiological action of the oligopeptides of this invention. The first is the binding of the oligopeptide to the cell surface at a receptor site, the second is the mitogenicity of the resulting product.

Figure 2:
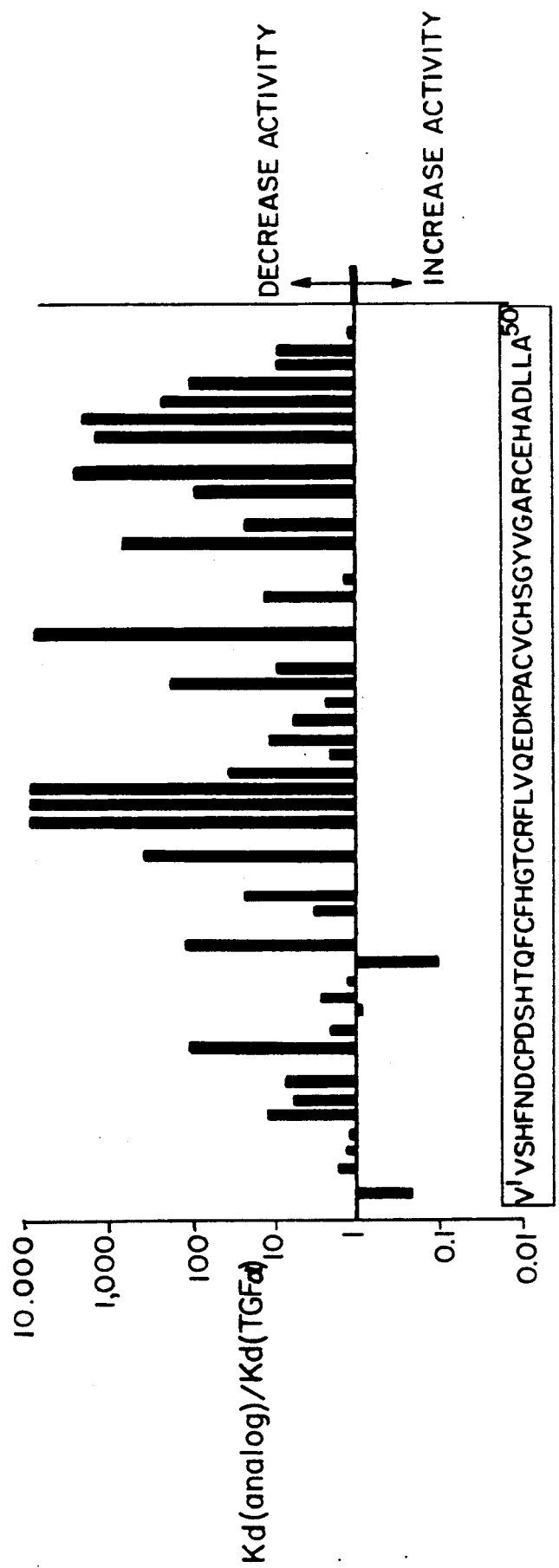
Figure 3:
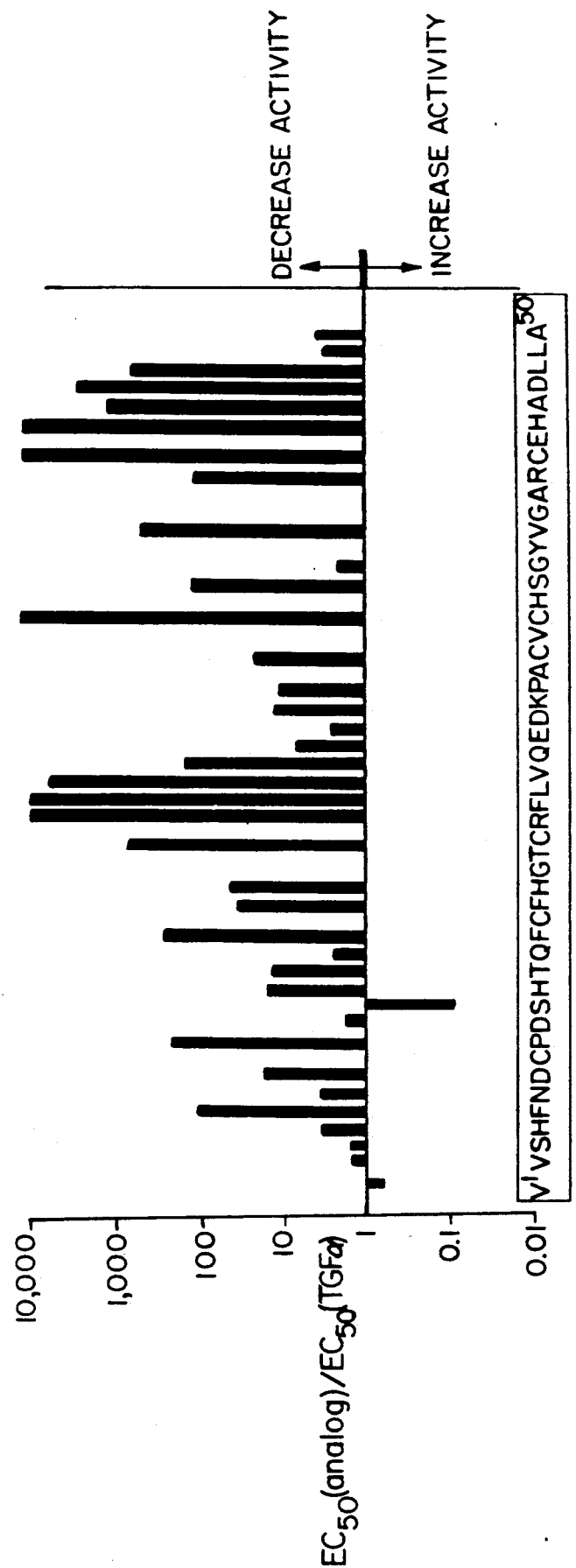

FIG. 2 shows the receptor binding activity of a number of modified TGFα oligopeptides in which the L-amino acid residue has been replaced with a D-amino acid residue. FIG. 3 shows the mitogenicity of certain of the modified products of FIG. 2. In both figures, the letters on the abscissa identify the amino acid residues according to the standard notation shown in Table 1. The ordinates of FIGS. 2 and 3 represent the relative activity of the modified TGFα compared to the natural product as determined by competitive EGF receptor and mitogenic assays.

Other products of the invention have been prepared in which an amino acid residue has been replaced, not with another form of the same acid, but with another amino acid residue. These include:

| | |
|---|---|
| (L—Ala-12)TGFα | (L—Ala-33)TGFα |
| (L—Ala-13)TGFα | (L—Ala-35)TGFα |
| (L—Ala-14)TGFα | (L—Ala-38)TGFα |
| (L—Ala-15)TGFα | (L—Ala-42)TGFα |
| (L—Ala-17)TGFα | (L—Ala-44)TGFα |
| (L—Ala-18)TGFα | (L—Ala-47)TGFα |
| (L—Ala-22)TGFα | (L—Ala-48)TGFα |
| (L—Ala-23)TGFα | (L—Ala-49)TGFα |
| (L—Ala-25)TGFα | (D—Phe-37)TGFα |
| (L—Ala-27)TGFα | (D—Phe-41)TGFα |

Taking into consideration such factors as receptor binding and mitogenicity the presently preferred compounds of the invention are:

| | |
|---|---|
| (D—Val-1)TGFα | (D—Gln-26)TGFα |
| (D—Val-2)TGFα | (D—Lys-29)TGFα |
| (D—Ser-3)TGFα | (D—Ala-50)TGFα |
| (D—Phe-5)TGFα | (L—Ala-35)TGFα |
| (D—Ser-11)TGFα | (D—Phe-37)TGFα |
| (D—Gln-14)TGFα | (D—Phe-41)TGFα |

The peptides of the invention are synthesized by the solid-phase method (1,2) using 4-(Boc-aminoacyloxymethyl)-phenylacetamidomethyl-resin (3,4). Typically, 0.1 to 0.4 g (0.4 mmol/g substitution) and prepared as described (4) were used. All syntheses are performed manually in a silanized reaction vessel using a mechanical shaker. All amino acids are protected with $N^\alpha$-tertbutyloxycarbonyl (Boc). Side chain protecting groups are: Arg(Tos), Asp(OcHex), Cys(4-MeBzl), Glu(OBzl), His(Dnp),Lys(2-CIZ), Ser(Bzl), Thr(Bzl), and Tyr(BrZ). Each synthetic cycle consists of (i) a 20-min deprotection with 50% trifluoracetic acid/$CH_2Cl_2$, (ii) neutralization with 5% diisopropylethylamine/$CH_2Cl_2$, and (iii) double coupling with preformed symmetrical anhydrides (3 equivalent of the Boc-amino acid) for 1 h each in $CH_2Cl_2$ and then in dimethylformamide (DMF). Couplings of Boc-Asn-OH, Boc-Gln-OH, and BocARg(Tos) are mediated by the preformed hydroxybenzotriazole active ester in DMF. Boc-Gly-OH is coupled with dicyclohexylcarbodiimide alone. All couplings are monitored by the quantitative ninhydrin test (5). A third coupling of symmetrical anhydride in N-methylpyrrolidinone at 50° C. for 2 h may be used when necessary to give >99.8% completion.

For removal from the resin, protected peptide-resin (0.2 to 0.4 g) is first treated 3-5 times with 1 M thiophenol in DMF for 2-6 h to remove the $N^{im}$-dinitrophenyl protecting group of His (6) and then with 50% trifluoroacetic acid/$CH_2Cl_2$ (10 ml) for 5 min to remove the $N^\alpha$-tertbutyloxycarbonyl group. The dried peptide-resin is treated with the low-high HF method of cleavage (7,8). For the low HF treatment, the peptide-resin is pre-mixed with dimethyl sulfide, p-thiocresol and p-cresol. Liquid HF at $-78°$ C. is then added to give a final volume of 10 ml (65:2.5:7.5:25, v/v). The mixture is equilibrated to 0° C. by stirring in an ice bath. After 2 h, the HF and dimethyl sulfide are removed in vacuo. The high HF treatment is initiated by recharging the reaction vessel at $-78°$ C. with 14 ml of fresh liquid HF to give a total volume of 15 ml of HF-p-cresol-p-thiocresol. The reaction is carried out at 0° C. for 1 h. After evaporation of HF at 0° C. and washing with cold ether-mercaptoethanol (99:1, v/v, 30 ml) to remove p-thiocresol and p-cresol, the crude reaction mixture is extracted with different buffers at the completion of the synthesis. For the linear and extended peptides as well as monocyclic peptides, acetic acid (10% by volume) or ammonium bicarbonate (0.5M) is used respectively for the extraction of basic and acidic peptides. For the bicyclic and tricyclic peptides, a solution (100 ml) of 8M urea 0.2M dithiothreitol in 0.1M Tris buffer, pH 8.0 is used.

The products are refolded to the oxidized forms by an improved and efficient refolding method (9), and purified to homogeneities by $C_{18}$ reverse-phase HPLC using a gradient of 5% $CH_3CN$ containing 0.045% $CF_3COOH$ and 60% $CH_3CN$ containing 0.039% $CF_3COOH$. The refolding strategy makes use of the thermodynamic nature of the EGF/TGFα structure and allowed then to refold to their most thermodynamic stable form under denaturing and constant disulfide reshuffling conditions. Essentially, the refolding method consists of two sequential gradients: a decreasing gradient of denaturants for refolding and an increasing gradient of oxidants for disulfide formation. Both processes are conducted in a single reaction vessel. A dialysis bag is best suited for minimizing loss due to handling and at the same time allowing the exclusion of the unwanted byproducts. Crude peptides (100-150 mg) are reduced, after HF cleavage, by 0.2M dithiothreitol in 8M urea, 0.1M Tris, pH 8.4. Refolding is conducted in a gradual gradient of reducing concentrations of urea under dialytic condition to remove dithiothreitol and other small molecules $Mr < 1000$ (18-36 hr). At 2M urea concentration, the peptide solution is diluted into 500 ml with Tris. HCl buffer and 1 mM of oxidized and 1 mM of reduced glutathione are added to initiate the second gradient refolding method increasing concentration of oxidized glutathione. To achieve this, the solution is slowly stirred in the presence of oxygen which serves to oxidize the glutathione, which also increases the concentration of oxidized glutathione to produce the desired oxidation potential of the solution. The disulfide formation may be monitored by HPLC and the peak corresponding to the refolded peptide usually elutes 3-5 min. earlier than the reduced form since the folded fold has a more compact structure than the reduced form. This simplified and highly efficient refolding procedure was found to be very useful.

The pharmaceutically useful products of this invention can be prepared in compositions containing pharmaceutically acceptable excipients for use in wound healing, ulcer therapy, and other traumas where rapid proliferation of normal cells is desired.

The compositions comprise effective amounts of the active ingredient together with the selected excipient and may be provided in solid, liquid, ointment, gel or other suitable form depending upon the selected method of administration.

Oral compositions may be provided in liquid form or as capsules, caplets or tablets. Liquid compositions containing the selected compound in suspension, emulsion or solution are together with coloring and/or flavoring agents, antioxidants, buffering agents or other ingredients normally found in such compositions are particularly useful.

The selected oligopeptide may be administered orally, parenterally or as a topical ointment, gel, or other suitable topical composition.

For parenteral application a product of the invention may be suspended in inert oil suitably a vegetable oil such as sesame, peanut or olive oil. Alternatively, a product may be suspended in an aqueous isotonic buffer solution at a pH of about 5.6 to 7.4.

REFERENCES (1) Merrifield, R. B. 1963. Solid phase peptide synthesis I. The synthesis of a tetrapeptide. J. Am. Chem. Soc. 85:2149-2154.

(2) Merrifield, R. B. 1986. Solid phase synthesis. Science 232:341-347.

(3) Mitchell, A. R., S. B. H. Kent, M. Engelhard, and R. B. Merrifield. 1978 J. Org. Chem. 43:2845-2852.

(4) Tam, J. P., S .B. H. Kent, T. W. Wong, and R. B. Merrifield. 1979. Improved synthesif of 4-(Boc-aminoacyloxymethyl)-phenylacetic acids for use in solid phase peptide synthesis. Synthesis 955-957.

(5) Sarin, V. K., S. B. H. Kent, J. P. Tam, and R. B. Merrifield. 1981. Quantitative monitoring of solid phase peptide synthesis by the ninhydrin reaction. Analytical Biochem. 117:147-157.

(6) Shaltiel, S., and M. Fridkin. 1970. Thiolysis of dinitrophenylimidazoles and its use during synthesis of histidine peptides. Biochem. 9:5122-5127.

(7) Tam, J. P., W. F. Heath, and R. B. Merrifield. 1983. $S_N2$ deprotection of synthetic peptides with a low concentration of HF in dimethylsulfide: evidence and application in peptide synthesis. J. Am. Chem. Soc. 105:6442-6455.

(8) Tam, J. P., W. F. Heath, and R. B. Merrifield. 1986. Mechanisms for the removal of benzyl protecting groups in synthetic peptides by trifluoromethanesulfonic acid-trifluoroacetic acid-dimethylsulfide. J. Am. Chem. Soc. 108:5242-5241.

(9) Ahmed, A. K., S. W. Schaffer, and D. B. Wetlaufer. 1975. Nonenzymatic reactivation of reduced bovine pancreatic ribonuclease by air oxidation and by glutathione oxidoreduction buffers. J. Biol. Chem. 250:8477-8482.

What is claimed is:

1. Transforming growth factor α modified by replacement of an L-amino acid residue with a D-amino acid residue.
2. (D-Val-1) TGFα.
3. (D-Val-2) TGFα.
4. (D-Ser-3) TGFα.
5. (D-Phe-5) TGFα.
6. (D-Ser-11) TGFα.
7. (D-Gln-14) TGFα.
8. (D-Gln-26) TGFα.
9. (D-Lys-29) TGFα.
10. (D-Ala-50) TGFα.
11. A pharmaceutical composition containing a therapeutically effective amount of transforming growth factor α modified by replacement of an L-amino acid residue with a D-amino acid residue together with a pharmaceutically acceptable excipient.

12. A pharmaceutical composition of claim 11 wherein the modified transforming growth factor is (D-Val-1) TGFα.

13. A pharmaceutical composition of claim 11 wherein the modified transforming growth factor is (D-Val-2) TGFα.

14. A pharmaceutical composition of claim 11 wherein the modified transforming growth factor is (D-Ser-3) TGFα.

15. A pharmaceutical composition of claim 11 wherein the modified transforming growth factor is (D-Phe-5) TGFα.

16. A pharmaceutical composition of claim 11 wherein the modified transforming growth factor is (D-Phe-5) TGFα.

17. A pharmaceutical composition of claim 11 wherein the modified transforming growth factor is (D-Gln-14) TGFα.

18. A pharmaceutical composition of claim 11 wherein the modified transforming growth factor is (D-Gln-26) TGFα.

19. A pharmaceutical composition of claim 11 wherein the modified transforming growth factor is (D-Lys-29) TGFα.

20. A pharmaceutical composition of claim 11 wherein the modified transforming growth factor is (D-Ala-50) TGFα.

* * * * *